US010881438B2

(12) United States Patent
Govey et al.

(10) Patent No.: US 10,881,438 B2
(45) Date of Patent: Jan. 5, 2021

(54) CLAVICLE FIXATION SYSTEM

(71) Applicant: GLOBUS MEDICAL, INC., Audubon, PA (US)

(72) Inventors: Peter Govey, Philadelphia, PA (US);
Stephanie Wolfe, Hatfield, PA (US);
Andrew Davison, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 257 days.

(21) Appl. No.: 15/719,633

(22) Filed: Sep. 29, 2017

(65) Prior Publication Data

US 2018/0256226 A1     Sep. 13, 2018

Related U.S. Application Data

(60) Provisional application No. 62/469,813, filed on Mar. 10, 2017.

(51) Int. Cl.
*A61B 17/80*     (2006.01)

(52) U.S. Cl.
CPC ...... *A61B 17/8061* (2013.01); *A61B 17/8004* (2013.01); *A61B 17/8014* (2013.01)

(58) Field of Classification Search
CPC . A61B 17/80; A61B 17/8004; A61B 17/8014; A61B 17/8052; A61B 17/8057; A61B 17/8061
See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |
| 3,716,050 A | 2/1973 | Johnston |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Eric S Gibson (57) ABSTRACT

Clavicle fixation devices and methods thereof. A clavicle fixation device including an elongated plate extending between first and second ends and defining a central portion, a first end portion between the central portion and the first end, and a second end portion between the central portion and the second end. The elongated plate has a contour which complements the contour of a clavicle anterior or superior surface. The elongated plate defines a plurality of spaced apart screw holes. The first end portion narrows moving from the central portion to the first end.

14 Claims, 12 Drawing Sheets

(56) References Cited

U.S. PATENT DOCUMENTS

| | | |
|---|---|---|
| 5,423,826 A | 6/1995 | Coates et al. |
| 5,601,553 A | 2/1997 | Trebing et al. |
| 5,676,667 A | 10/1997 | Hausman |
| 5,709,686 A | 1/1998 | Talos et al. |
| 5,718,704 A | 2/1998 | Medoff |
| 5,746,742 A | 5/1998 | Runciman et al. |
| 5,785,712 A | 7/1998 | Runciman et al. |
| 5,938,664 A | 8/1999 | Winquist et al. |
| 6,001,099 A | 12/1999 | Huebner |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| 6,533,786 B1 | 3/2003 | Needham et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 * | 7/2007 | Orbay ............... A61B 17/8057 606/291 |
| 7,294,130 B2 | 11/2007 | Orbay |
| 7,322,983 B2 | 1/2008 | Harris |
| 7,341,589 B2 | 3/2008 | Weaver et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,695,472 B2 | 4/2010 | Young |
| 7,722,653 B2 | 5/2010 | Young et al. |
| 7,740,648 B2 | 6/2010 | Young et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 * | 3/2013 | Ralph ............... A61B 17/80 606/280 |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,551,095 B2 * | 10/2013 | Fritzinger .......... A61B 17/8014 606/280 |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 * | 10/2015 | Fritzinger .......... A61B 17/8014 |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |

(56) References Cited

U.S. PATENT DOCUMENTS

| | | |
|---|---|---|
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 * | 4/2016 | Chan .................. A61B 17/1728 |
| 9,320,554 B2 * | 4/2016 | Greenberg .......... A61B 17/8061 |
| 9,322,562 B2 | 4/2016 | Takayama et al. |
| 9,370,388 B2 | 6/2016 | Globerman et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,566,097 B2 | 2/2017 | Fierlbeck et al. |
| 9,636,157 B2 | 5/2017 | Medoff |
| 9,649,141 B2 | 5/2017 | Raven, III et al. |
| 9,668,794 B2 | 6/2017 | Kuster et al. |
| 2002/0045901 A1 | 4/2002 | Wagner et al. |
| 2004/0097937 A1 * | 5/2004 | Pike ........................ A61B 17/80 606/282 |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0241607 A1 | 10/2006 | Myerson et al. |
| 2007/0270849 A1 | 11/2007 | Orbay et al. |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0059424 A1 * | 3/2012 | Epperly ............. A61B 17/8061 606/281 |
| 2012/0323284 A1 | 12/2012 | Baker et al. |
| 2013/0018426 A1 | 1/2013 | Tsai et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0371798 A1 * | 12/2014 | Platt ....................... A61B 17/80 606/281 |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 * | 3/2015 | Marotta .............. A61B 17/8014 606/281 |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 * | 7/2015 | Sixto, Jr. ............ A61B 17/8057 606/289 |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 * | 10/2016 | Sixto ................... A61B 17/808 |
| 2016/0324552 A1 | 11/2016 | Baker et al. |
| 2016/0354122 A1 | 12/2016 | Montello et al. |
| 2017/0035478 A1 * | 2/2017 | Andermahr ........ A61B 17/8057 |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0215931 A1 | 8/2017 | Cremer et al. |
| 2018/0049782 A1 * | 2/2018 | Gahman ................ A61B 17/80 |
| 2018/0049785 A1 * | 2/2018 | Langdale ........... A61B 17/8042 |
| 2018/0161081 A1 * | 6/2018 | Anding ................ A61B 17/80 |
| 2018/0256224 A1 * | 9/2018 | Govey ............... A61B 17/8014 |
| 2018/0256226 A1 * | 9/2018 | Govey ............... A61B 17/8061 |
| 2018/0310972 A1 * | 11/2018 | Anding ............... A61B 17/8014 |
| 2019/0269443 A1 * | 9/2019 | Laird, Jr. ........... A61B 17/8061 |
| 2019/0269446 A1 * | 9/2019 | Laird, Jr. ........... A61B 17/8057 |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| FR | 2846870 A1 | 5/2004 |
| FR | 2928259 A1 | 9/2009 |
| FR | 3003749 A1 | 10/2014 |
| JP | 2003210478 A | 7/2003 |
| TW | 201316942 A | 5/2013 |
| WO | 2016079504 A1 | 5/2016 |

* cited by examiner

CLAVICLE FIXATION SYSTEM

CROSS REFERENCE TO RELATED APPLICATION

This application claims priority to U.S. provisional application No. 62/469,813, filed Mar. 10, 2017, which is incorporated by reference herein in its entirety for all purposes.

FIELD OF THE INVENTION

The present disclosure is generally directed to surgical devices and methods. More particularly, the present disclosure is directed to trauma plates, fasteners, intramedullary nails, systems, and methods designed to fix fractures, nonunions, and ligamentous injuries of the clavicle or the like.

BACKGROUND

The clavicle or collar bone is one of the most commonly broken bones in the body. While some clavicle fractures heal with nonoperative management, more recent studies have found that in cases of specific fracture patterns and locations, not all clavicle fractures behave the same way.

The focus of treatment of middle third fractures remains nonoperative, although evidence is mounting in support of operative treatment for displaced midshaft clavicle fractures. The incidence of nonunion of displaced distal third fractures is high, and current recommendations are to fix these injuries surgically.

Patients with the following injuries, for example, are often considered for operative intervention: complete fracture displacement, severe displacement causing tenting of the skin with the risk of puncture, fractures with significant shortening, comminuted fractures with a displaced transverse zed fragment, fractures with neurovascular compromise, displaced medial clavicular fractures with mediastinal structures at risk, polytrauma with multiple fractures, open fractures, fractures where the patient has an inability to tolerate closed treatment, fractures with interposed muscle, established symptomatic nonunion, or concomitant glenoid neck fracture.

Additionally, evidence is mounting in support of operative treatment for displaced midshaft clavicle fractures, finding that operative repair for these injuries provided better results than did nonoperative treatment. In several studies, outcomes with regard to the rate of successful bone union, functional outcome, time required for patients to resume their daily activities, and overall patient satisfaction were superior in the operative group than in nonoperative patients. There was also significantly less posttraumatic clavicular shortening in the surgical group.

With an increased consideration of operative repair, improved clavicle fixation systems are desired.

SUMMARY

Clavicle bone plates, intramedullary clavicle nails, systems, and methods of treatment are provided. The systems and devices may be particularly suitable for fixation of the clavicle. Although generally described with reference to the clavicle, it will be appreciated that the systems and devices may be adapted for use with any long bone, short bone, or flat bone.

In at least one embodiment, the present disclosure provides a clavicle fixation device including an elongated plate extending between first and second ends and defining a central portion, a first end portion between the central portion and the first end, and a second end portion between the central portion and the second end. The elongated plate has a contour which complements the contour of a clavicle anterior or superior surface. The elongated plate defines a plurality of spaced apart screw holes. The first end portion narrows moving from the central portion to the first end. The second end portion narrows moving from the central portion to the second end. In at least one embodiment, the second portion widens before narrowing.

In at least one embodiment, the present disclosure provides a clavicle fixation device including an elongated plate extending between first and second ends and having a contour which complements the contour of a clavicle superior surface. The elongated plate defines a plurality of spaced apart screw holes. A hook member extends from the first end of the elongated plate. The hook member includes an extension portion extending from the first end of the elongated plate, a descending arm extending inferiorly from the extension portion to a given depth, and a lateral arm angling laterally from the descending arm.

In at least one embodiment, the present disclosure provides a clavicle fixation device including an elongated body extending from a trailing end to a medial leading end and having an anatomically appropriate radius at the medial leading end. The medial leading end defines a pointed shape with flats on each side of a rounded tip, the rounded tip extending to a widened underside.

Also provided are methods of treatment and kits including bone plates and/or intramedullary nails of varying shapes and sizes, bone anchors, fasteners, insertion tools, and other components for installing the same.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

Orthopedic bone plates, intramedullary nails, systems, and methods of treatment are provided. The bone plates and nails may be useful in repair of the clavicle. Although further described with reference to treatment of the clavicle, it will be appreciated that the system and devices may be adapted for use with any bones, including but not limited to, the femur, tibia, humerus, fibula, ulna, radius, bones of the foot, bones of the hand, or the like.

Figure 1:
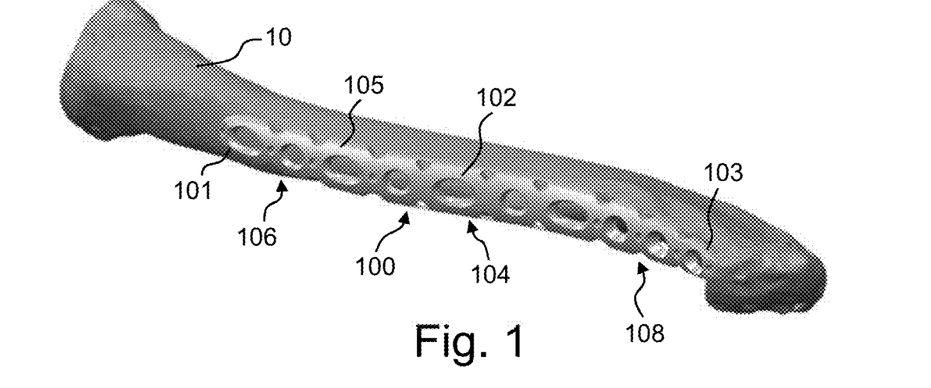
FIG. 1 is a perspective view of an anterior fixation plate in accordance with one embodiment of the present disclosure shown positioned along a clavicle.
Figure 3:
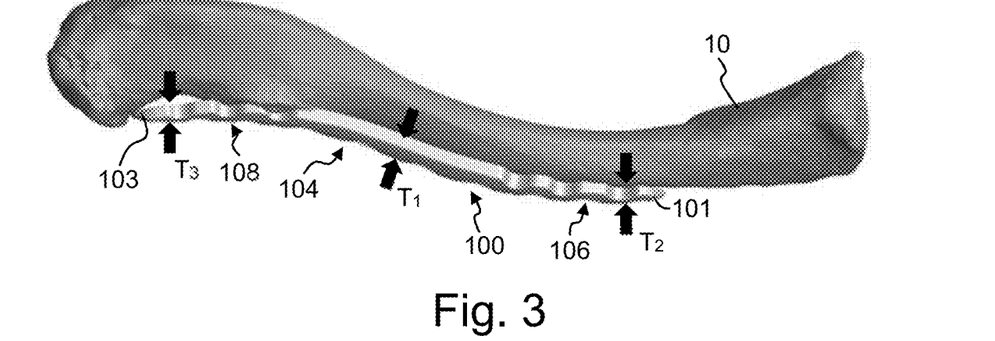
FIG. 3 is a top plan view of the anterior fixation plate of FIG. 1.
Figure 4:
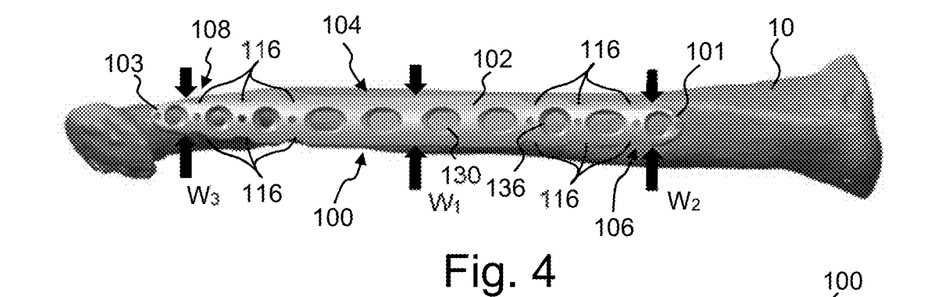
FIG. 4 is a front elevation view of the anterior fixation plate of FIG. 1.

Referring to FIGS. 1-19, anterior fixation plates 100, 100', 100" in accordance with various embodiments of the disclosure will be described. FIGS. 1, 3 and 4 illustrate an anterior fixation plate 100 positioned along an anterior surface of a clavicle 10. The anterior fixation plate 100 includes an elongate body 102 extending between opposed ends 101, 103 with an outer surface 105 and an inner, bone contacting surface 107.

Figure 2A:
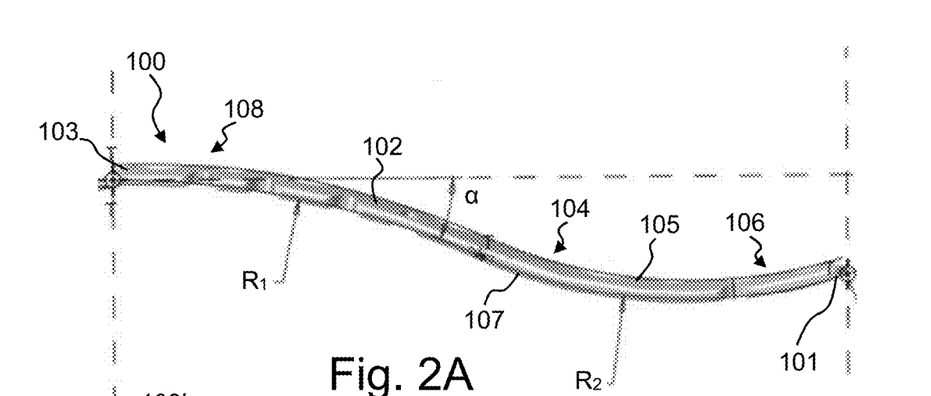
FIGS. 2A and 2B are side elevation views of two anterior fixation plates in accordance with an embodiment of the disclosure illustrating different contours.
Figure 2B:
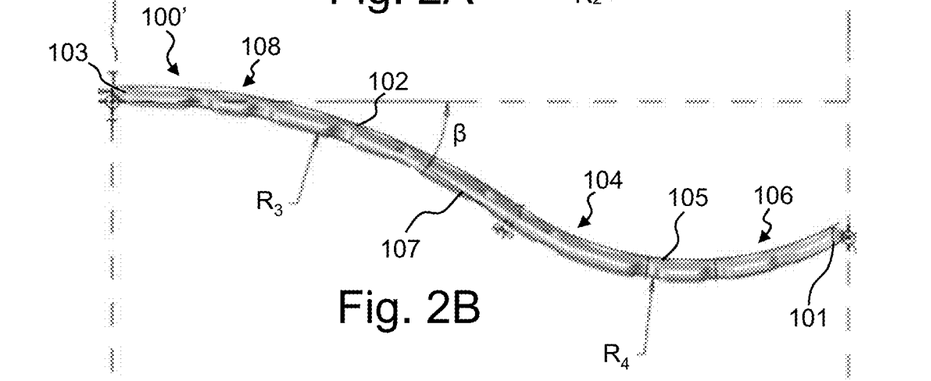

Referring to FIGS. 2A and 2B, the anterior plates 100, 100' are anatomically contoured to fit along the curved anatomy of the anterior clavicle. The anterior plates 100, 100' are interchangeable for left-side and right-side clavicles. As the curvature of the bone varies between individuals, the anterior plates 100, 100' are offered in multiple contours, with two exemplary contours illustrated in FIGS. 2A and 2B. Each plate 100, 100' includes a central portion 104 extending between end portions 106, 108. The contour of the plate 100, 100' is defined by the angle $\alpha$, $\beta$ of the end portions 106, 108 relative to the central portion 104 as well as the curvature $R_1$, $R_2$, $R_3$, $R_4$ of each end portion 106, 108. The angle α of plate 100 may range, for example, from about 20-30°, about 20-25°, about 23-25°, or about 24°. The angle β of plate 100' may range, for example, from about 30-40°, about 30-35°, about 33-35°, or about 34°. The radius $R_1$, may range, for example, from about 100-200 mm, about 120-160 mm, or about 140 mm. The radius $R_2$ may range, for example, from about 10-100 mm, about 60-100 mm, or about 80 mm. The radius $R_3$ may range, for example, from about 50-150 mm, about 90-130 mm, or about 110 mm. The radius $R_4$ may range, for example, from about 10-100 mm, about 30-70 mm, or about 50 mm. In the illustrated embodiments, the angle α of plate 100 (for example 24°) is smaller than the angle β of plate 100' (for example 34°) and the radiuses $R_1$, $R_2$ (for example 140 mm, 80 mm) are larger than the radiuses $R_3$, $R_4$ (for example 110 mm, 50 mm). With the illustrated configurations, the plate 100 of FIG. 2A is said to have a shallow configuration while the plate 100' of FIG. 2B is said to have a deep configuration. The plates 100, 100' may have various angles and radiuses or elliptical dimensions and are not limited to the illustrative examples. Selecting a contoured plate 100, 100' closely matching the bone's contour minimizes plate prominence and irritation under soft tissue.

Figure 5:
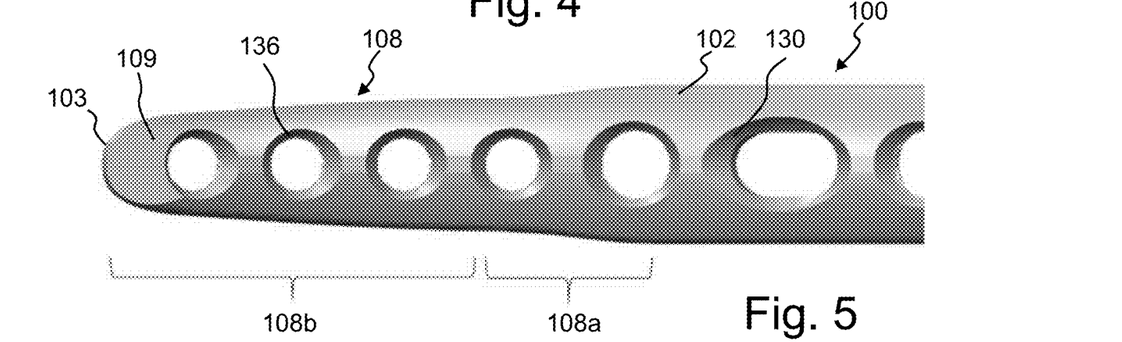
FIG. 5 is a plan view of an end portion of an anterior fixation plate in accordance with an embodiment of the disclosure.
Figure 6:
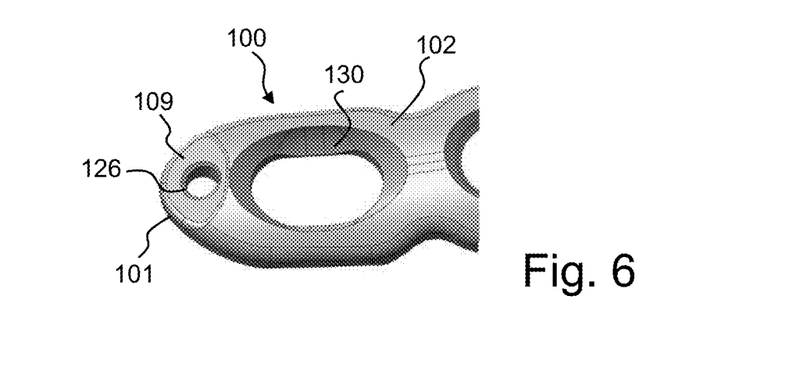
FIG. 6 is a perspective view of an end tip of an anterior fixation plate in accordance with an embodiment of the disclosure.
Figure 7:
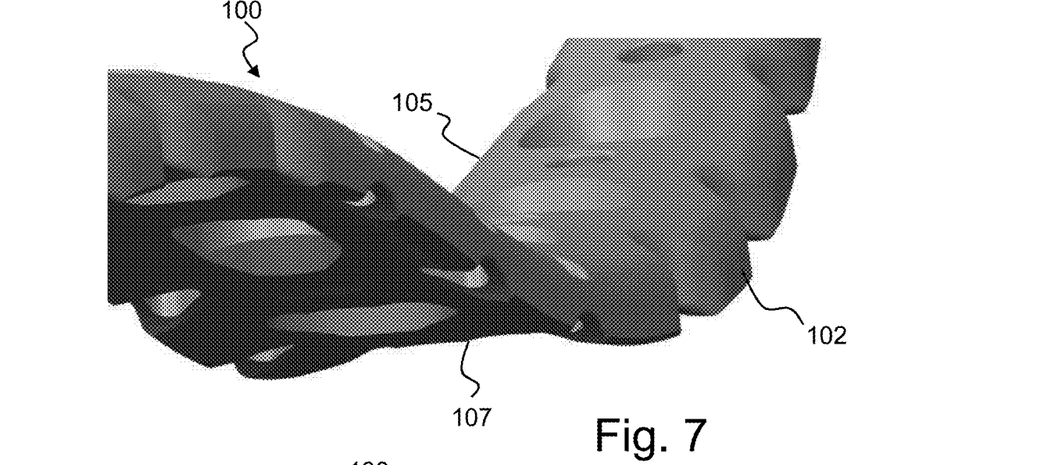
FIG. 7 is a perspective view of a portion of an anterior fixation plate in accordance with an embodiment of the disclosure illustrating the rounded top and undersides thereof.
Figures 8, 9:
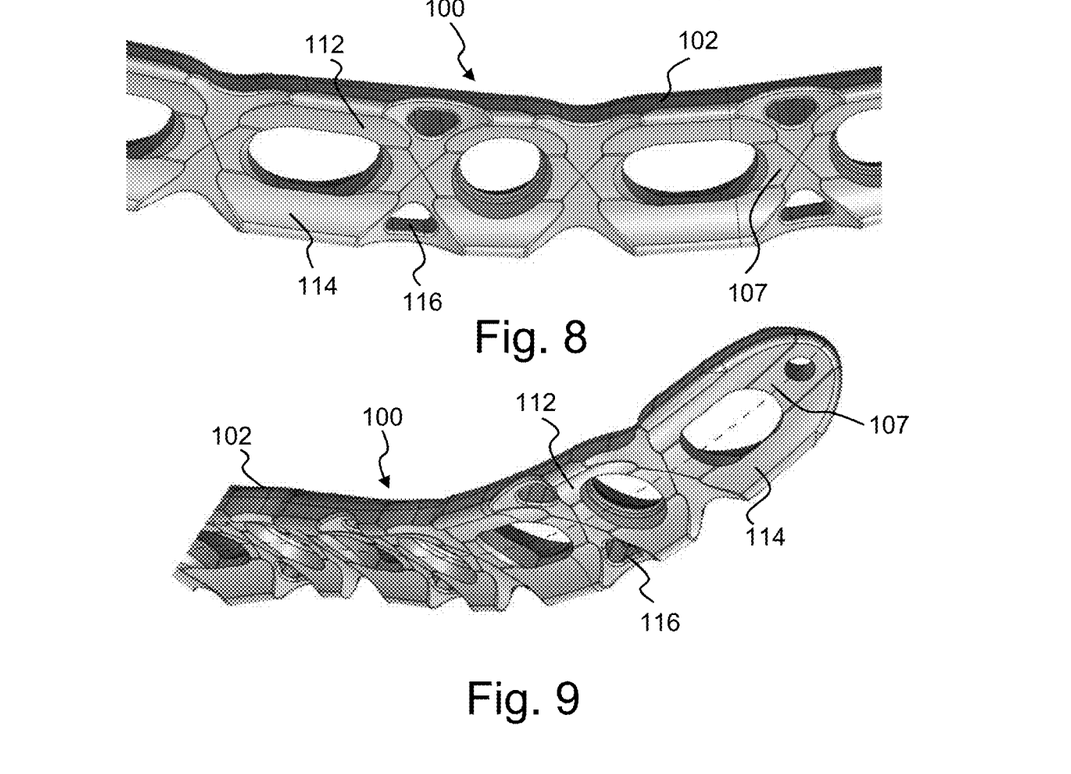
FIG. 8 is a perspective view of the underside of a central portion of an anterior fixation plate in accordance with an embodiment of the disclosure.
FIG. 9 is a perspective view of the underside of an end portion of the anterior fixation plate of FIG. 8.

Referring to FIGS. 3-6, the anterior fixation plate 100 is further contoured in both width and cross-sectional thickness. In the illustrated embodiment, the plate 100 has a largest cross-sectional thickness $T_1$ in the central portion 104 and then tapers to smaller cross-sectional thickness $T_1$, $T_3$ in each end portion 106, 108. The thicknesses $T_2$, $T_3$ in the end portions 106, 108 may be the same or distinct from one another. As illustrated in FIGS. 5 and 6, the plate 100 may include additional taper 109 at the plate ends 101, 103, beyond the last hole. The additional taper 109 aids sub-muscular insertion of the plate for minimally-invasive procedures.

The plate 100 also has a largest width $W_1$ in the central portion 104 and then narrows to smaller widths $W_2$, $W_3$ in each end portion 106, 108. The widths $W_2$, $W_3$ in the end portions 106, 108 may be the same or distinct from one another. Referring to FIG. 5, in the illustrated embodiment, the end portion 108 narrows at different rates, with the portion 108a closest to the central portion 104 narrowing more steeply than the portion 108b toward the end 103, which has a more gradual narrowing.

The plate 100 thicknesses and widths are selected such that the plate 100 optimally spans a common clavicle fracture zone. Image research study of clavicle fractures is used to identify the most common fracture zones. The length, thicknesses and width of each plate portion 104, 106, 108 are selected such that the optimal span comprises a thicker cross-sectional area and greater moment of inertia for a distance appropriate to the extent of the fracture zone. At either end of the optimal span, where strength is less essential, the plate 100 narrows in width and tapers lower in thickness. This narrowing and taper enables the plate 100 to be low-profile, minimizing prominence and irritation under soft tissue.

Referring to FIGS. 7-11, the plate 100 may also include a rounded outer surface 105 and a rounded inner surface 107. The rounded surfaces 105, 107 assist in keeping plate prominence to a minimum. The inner surface 107 may further include cylindrical or elliptical undercuts 112, 114 sweeping the length of the plate 100. The undercuts 112, 114 reduce the contact surface of the plate 100 against the clavicle bone 10. This may reduce damage to the periosteum, preserve blood supply, reduce osteonecrosis, and speed fracture consolidation.

Figure 10:
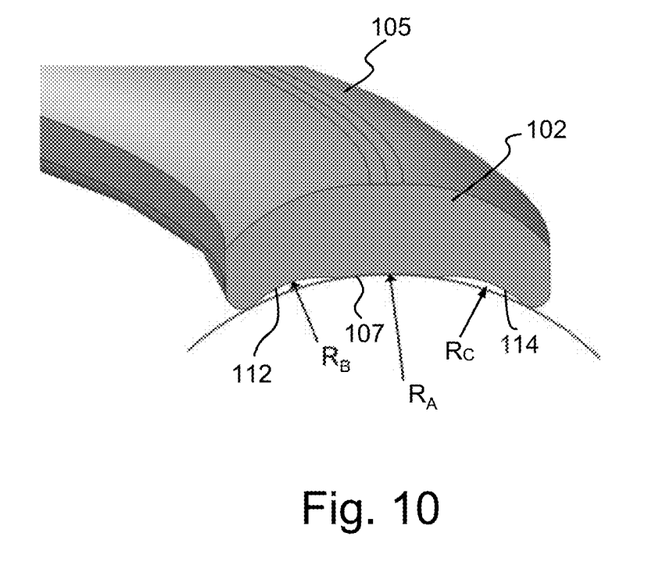
FIG. 10 is a top perspective view illustrating the cross-sectional profile of a fixation plate in accordance with an embodiment of the disclosure.
Figure 11:
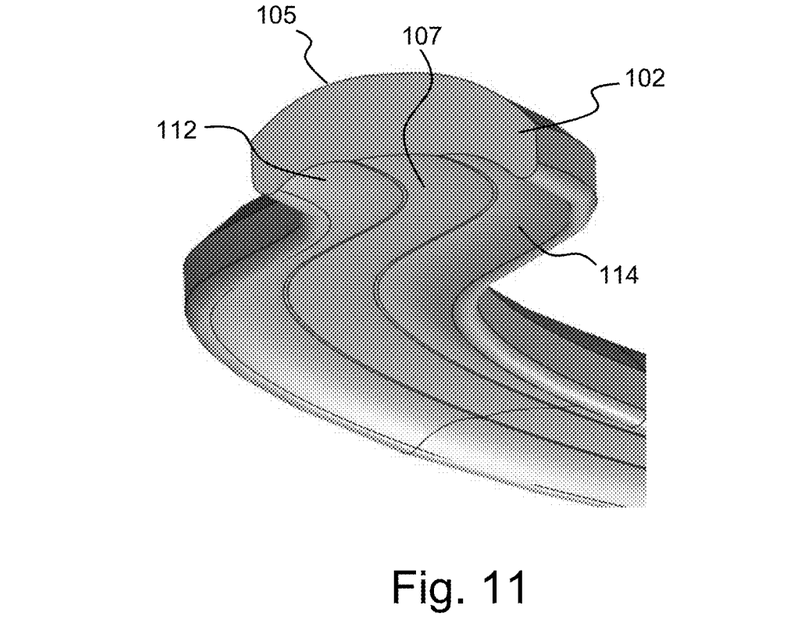
FIG. 11 is a bottom perspective view illustrating the underside of the cross-sectional profile of FIG. 10.

Referring to FIGS. 10 and 11, an exemplary undercut pattern is illustrated. The plate inner surface 107 has a curvature with a radius of $R_A$ and defines the bone contacting surface. The radius $R_A$ is similar to the radius of the clavicle bone surface. Each of the undercuts 112, 114 extends the length of the plate 100 and has a radius $R_B$, $R_C$, respectively. The radiuses $R_B$, $R_C$ may be the same or may be different from one another. The radiuses $R_B$, $R_C$ of the undercuts 112, 114 are smaller than the radius containing the plate/bone contact surfaces $R_A$. The undercuts 112, 114 reduce plate contact with the bone surface while only minimally reducing cross-sectional strength. While two undercuts are illustrated, more or fewer undercuts, either circular or elliptical, may be utilized.

Figure 12:
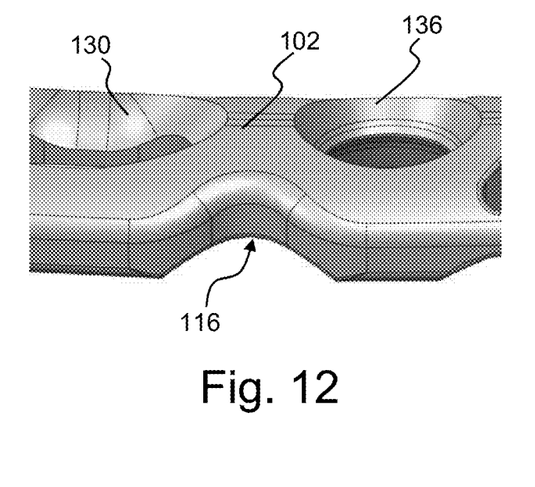
FIG. 12 is a side perspective view of a portion of an anterior fixation plate in accordance with an embodiment of the disclosure illustrating the side relief cuts thereof.
Figure 13:
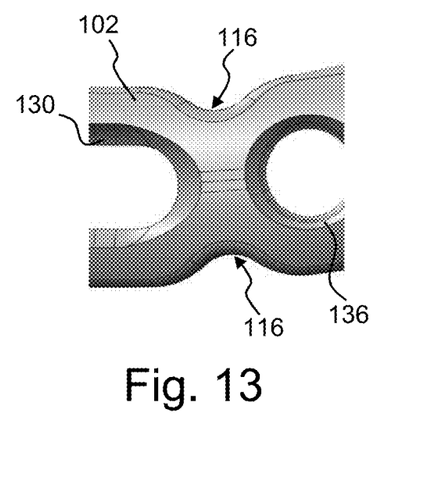
FIG. 13 is a plan view illustrating the side relief cuts of FIG. 12.

Referring to FIGS. 12 and 13, side relief cuts 116 extend into the body 102 of the plate 100 along the sides thereof. In the illustrated embodiments, the relief cuts 116 are provided in opposed pairs on each side of the body 102, however, other configurations may be utilized. The relief cuts 116 are positioned between screw holes thereby reducing the moment of inertia between the screw holes to allow preferential bending between holes, helping to minimize deformation of the screw holes. The illustrated relief cuts 116 have a rounded or smooth configuration to minimize the risk of kinking or fracture. As illustrated in FIGS. 1, 4, 14 and 15, the relief cuts 116 are present near the end portions 106, 108 of the plate 100 where contour customization by bending is the most likely to be desired, however, other configurations may be utilized.

Figure 14:
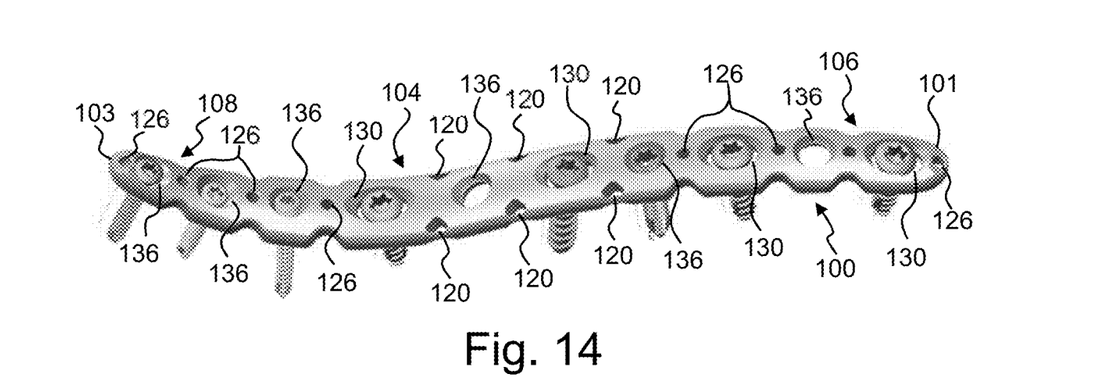
FIG. 14 is a perspective view of the anterior lateral fixation plate of FIG. 1.

Referring to FIGS. 14-19, the plates 100, 100" may be provided with various through holes, including oblong suture holes 120, round K-wire holes 126, dynamic compression plating (DCP) slots 130, and polyaxial holes 136. The oblong suture holes 120 are positioned along but inward of the side edges of the plate body 102. The round K-wire holes 126 are provided at each end 101, 103 of the plate 100, 100" and may be provided at other more central areas, as shown in FIG. 14. The oblong suture holes 120 and the round K-wire holes 126 may be used as K-wire holes to allow provisional fixation of the plate 100, 100" with K-wires. Additionally, the oblong suture holes 120 may be used for suture and an undercut 122 is aligned with each oblong suture hole 120 and extends into the inner surface 107 of the plate 100, 100". The undercuts 122 have a width that is wider than the width of the corresponding suture hole 120. The undercuts 122 enable free passage of suture underneath the plate 100, 100" without interference at the plate/bone interface. The undercuts 122 help reduce the moment of inertia between screw holes to allow preferential bending between holes, helping to minimize deformation of screw holes. This is useful for plate contour customization. The undercuts 122 also serve to further reduce the contact surface of the inner surface 107 of the plate 100, 100". The undercuts 122 may be co-located with relief cuts 116 and suture holes 120.

In the illustrated embodiment, the oblong suture holes 120 have a rounded triangular configuration and are positioned between screw holes 130, 136. With this configuration, the oblong suture holes 120 reduce the moment of inertia between screw holes to allow preferential bending between holes, helping to minimize deformation of screw holes. This is useful for plate contour customization. While the oblong suture holes 120 are illustrated with a rounded triangular configuration, other configurations may be utilized, for example, elliptical, round, oval.

The oblong suture holes 120 also facilitate passage of suture/needles to serve as anchor points useful for reattachment and repositioning of soft tissue damaged during surgery which may aid post-surgical soft tissue healing. The oblong suture holes 120 also facilitate passage of suture/needles for cerclage techniques which may aid in reduction and fixation of bone fragments, particularly "butterfly" fragments on the inferior side of the bone. In the illustrated embodiment, the opposed suture holes 120 on either side of the plate 100, 100" allow for cerclage running from one side of the plate, down under the bone, up to the opposing suture hole, and potentially across again to the originating hole for successive loops. These opposing holes 120 also aid cerclage perpendicular to the plate trajectory. This is the optimal angle for applying force to reduce fragments toward the plate.

Figure 16:
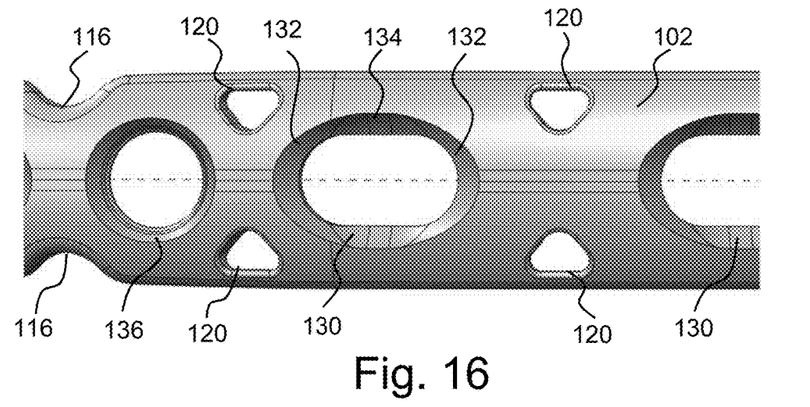
FIG. 16 is a plan view of a central portion of an anterior fixation plate in accordance with an embodiment of the disclosure
Figure 17:
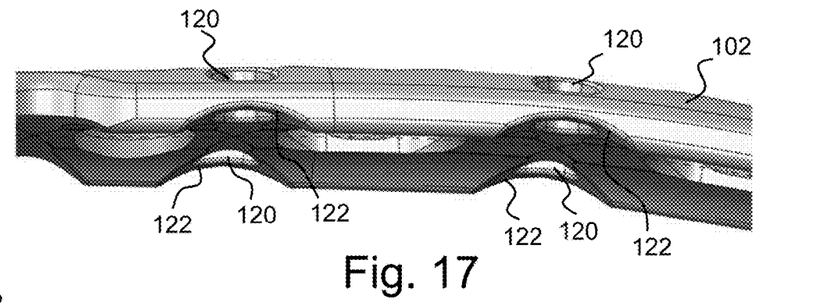
FIG. 17 is a side perspective view of the anterior fixation plate of FIG. 16.
Figure 18:
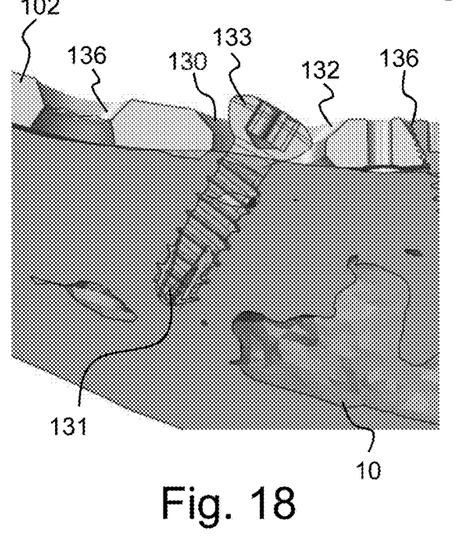
FIG. 18 is a cross-sectional view of a portion of an anterior fixation plate in accordance with an embodiment of the invention illustrating a screw extending through a dynamic compression plating slot thereof.

Referring to FIGS. 16 and 18, each DCP slot 130 has an oblong configuration with tapered end walls 132 and a central neutral head receiving area 134. Contact of a screw head 133 with the tapered end wall 132 may cause medial-lateral motion of the plate 100, 100" relative to the bone to compress a bone fracture. Standard neutral placement may also be achieved by positioning the screw head in the central neutral head receiving area 134. Compression or neutral placement is typically achieved using a non-locking screw 131, for example, a 3.5 mm non-locking screw. The DCP slot 130 also enables off-axis, or oblique, screw trajectories in the plane of the slot using non-locking screws. Cancellous screws enable oblique or neutral screw trajectories through the DCP slot 130, useful for fragment capture or load neutralization across the fracture line.

Figure 19:
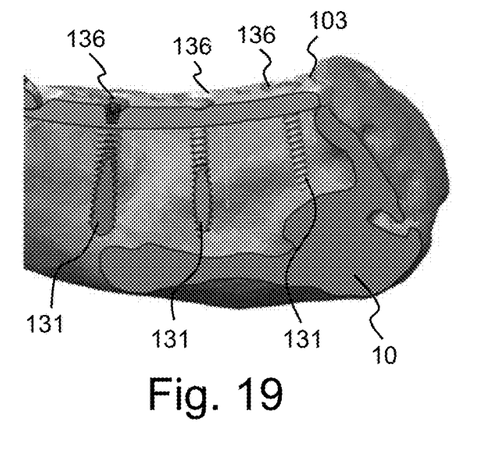
FIG. 19 is a cross-sectional view of a portion of an anterior fixation plate in accordance with an embodiment of the invention illustrating screws extending through polyaxial holes thereof.

The polyaxial holes 136 accept locking and non-locking screws, both inserted within a cone of angulation, as illustrated in FIG. 18. The polyaxial holes 136 may be configured to accept different sized screws, for example, 3.5 mm screws at the midshaft end 101 of the plate 100 and 2.5 mm screws at the far lateral end 103 of the plate 100. The nominal trajectory of the far lateral holes assists in aiming screws to good quality bone and away from the acromioclavicular joint space, as illustrated in FIG. 19.

Figure 15:
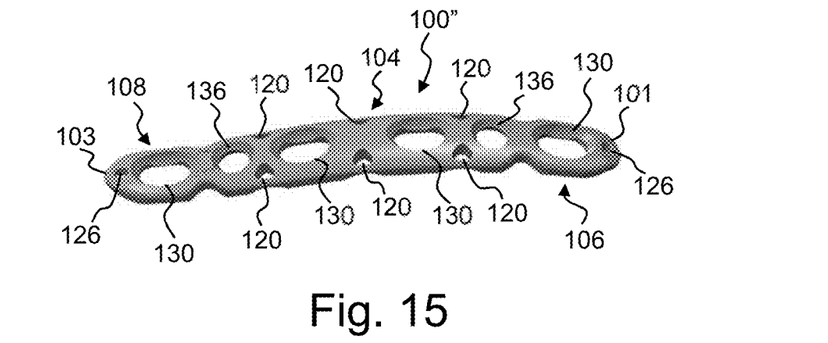
FIG. 15 is a perspective view of an anterior midshaft fixation plate in accordance with an embodiment of the disclosure.

As illustrated in FIGS. 14 and 15, the DCP slots 130 and polyaxial holes 136 may be arranged in various configurations. In the anterior lateral plate 100 illustrated in FIG. 14, the DCP slots 130 and the polyaxial holes 136 alternate in the central portion 104 and the end portion 106 while the end portion 108 includes consecutive polyaxial holes 136. In the anterior midshaft plate 100" illustrated in FIG. 15, the DCP slots 130 and the polyaxial holes 136 alternate over the length of the plate 100". Other configurations other than those illustrated may also be utilized.

Figure 20:
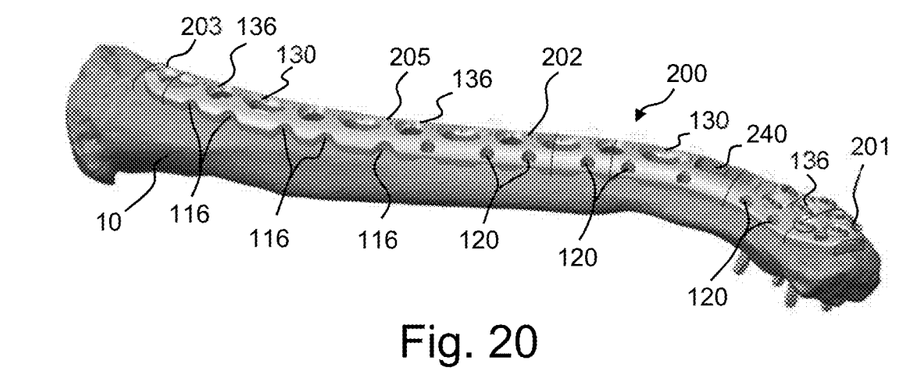
FIG. 20 is a perspective view of a superior fixation plate in accordance with one embodiment of the present disclosure shown positioned along a clavicle.

Referring to FIGS. 20-28, superior fixation plates 200, 200', 200", 200' in accordance with various embodiments of the disclosure will be described. FIG. 20 illustrates a superior fixation plate 200 positioned along a superior surface of a clavicle 10. The superior fixation plates 200, 200', 200", 200' are similar to the anterior fixation plates described above and include an elongate body 202 extending between opposed ends 201, 203 with an outer surface 205 and an inner, bone contacting surface 207. The superior fixation plates 200, 200', 200", 200' may include any of the features described with respect to the anterior plates, including rounded outer and inner surfaces 205, 207, undercuts 112, 114 on the inner surface 207, side relief cuts 116, oblong suture holes 120, undercuts 122, round K-wire holes 126, DCP slots 130 and polyaxial holes 136.

Figure 21A:
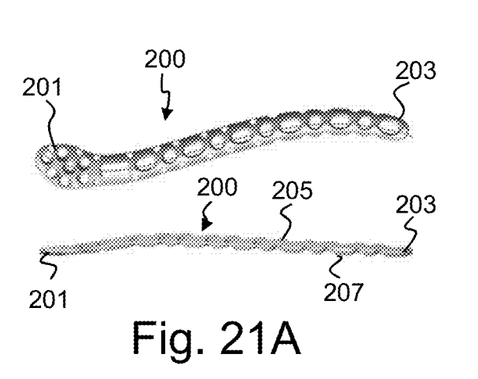
FIGS. 21A and 21B are top and side elevation views of two superior fixation plates in accordance with an embodiment of the disclosure illustrating different contours.
Figure 21B:
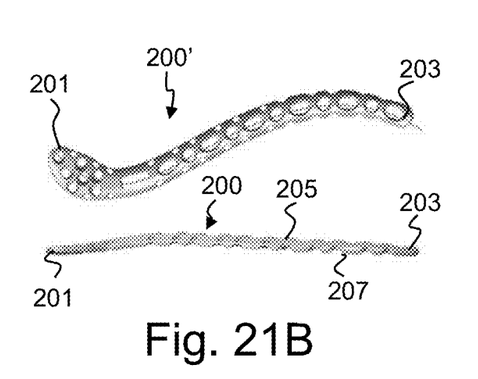

Referring to FIGS. 21A and 21B, the superior plates 200, 200' are anatomically contoured to fit along the curved anatomy of the superior clavicle. The superior plates 200, 200' are not interchangeable for left-side and right-side clavicles, but instead are configured for either the left-side or right-side clavicle. As the curvature of the bone varies between individuals, the superior plates 200, 200' are offered in multiple contours, with two exemplary contours illustrated in FIGS. 21A and 21B. Each plate 200, 200' has an "S" curvature in the A/P direction and a slight bow in the caudal/cranial direction. Plates 200, 200' following contours with less (FIG. 21A) or more (FIG. 21B) "S" curvature may be referred to as "shallow" or "deep" contoured plates, respectively.

Figure 22:
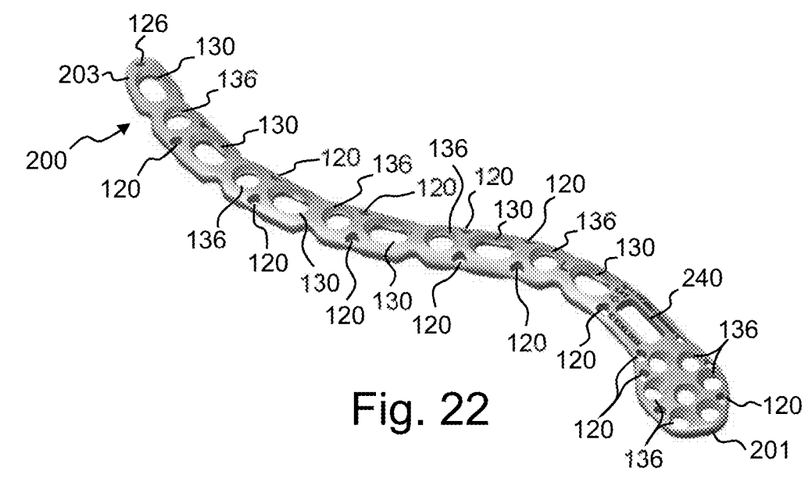
FIG. 22 is a perspective of the superior fixation plate of FIG. 20.
Figure 23:
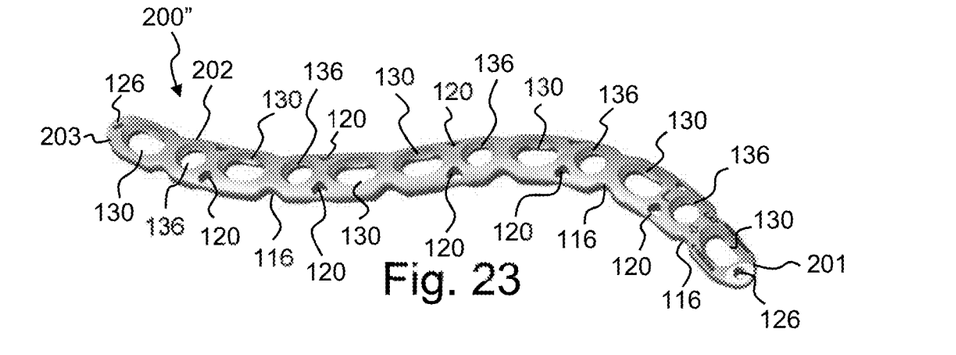
FIG. 23 is a perspective view of another superior fixation plate in accordance with an embodiment of the present disclosure.
Figure 24:
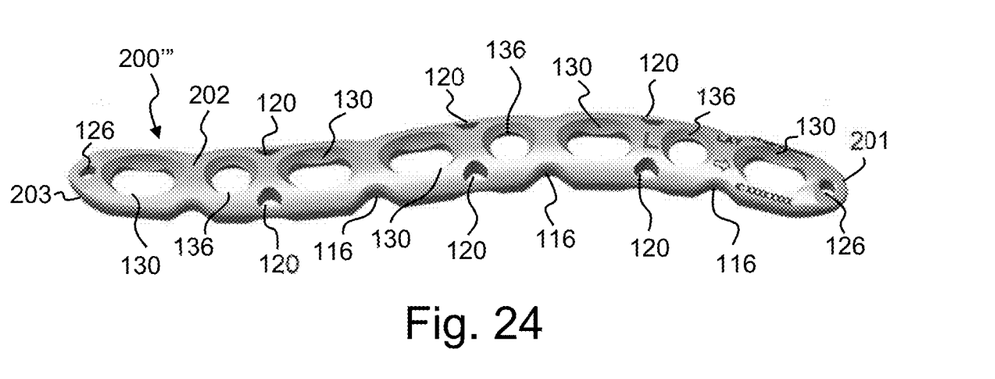
FIG. 24 is a perspective view of another superior fixation plate in accordance with an embodiment of the present disclosure.
Figure 25:
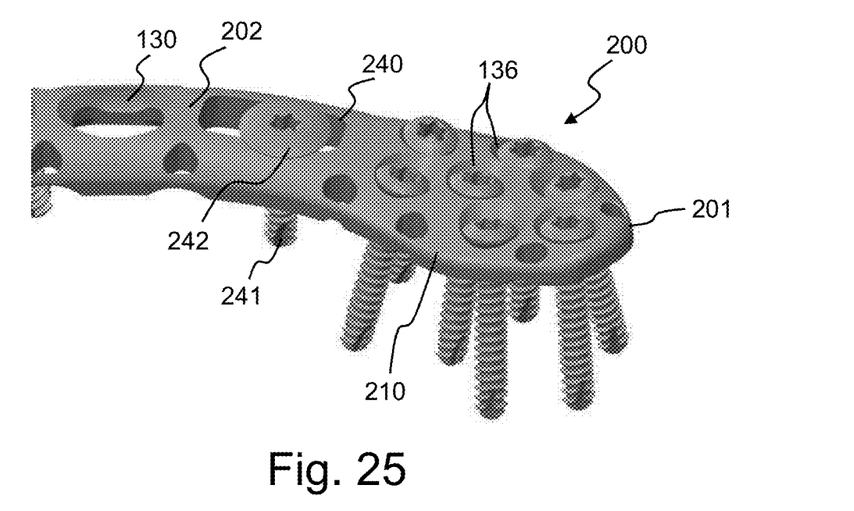
FIGS. 25 and 26 are top and side perspective views, respectively, of an end portion of a superior fixation plate in accordance with an embodiment of the disclosure illustrating a plurality of screws extending through the polyaxial holes thereof.

Furthermore, as shown in FIGS. 22-24, the plates 200, 200", 200' may have varying lengths with varying hole configurations. FIGS. 22 and 23 show superior lateral plates 200, 200" having a length longer than the length of the superior midshaft plate 200' illustrated in FIG. 24. Each of the plates 200, 200", 200''' generally include alternating DCP slots 130 and polyaxial holes 136, however, other hole configurations may be utilized. The superior fixation plate 200 includes an additional hole, namely, a sliding slot 240. Referring to FIG. 25, the sliding slot 240 has a rectangular configuration and is configured to receive a sliding slot screw 241 with a wide head 242. The shaft of the screw 241 has a diameter smaller than the width of the slot 240 while the head 242 has a diameter greater than the width of the slot 240. The slot 240 allows fine bi-directional adjustments of the plate 200 while maintaining provisional placement. The screw 241 may also be utilized for permanent fixation. The sliding slot screw and all other screws in the set may also be utilized as a stand-alone fragment capture/lag screw.

Figure 26:
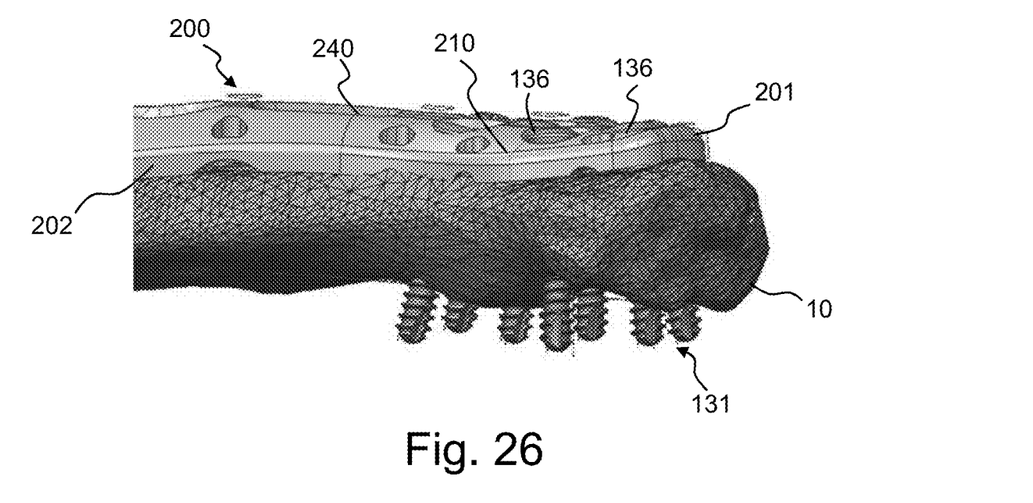
Figure 27:
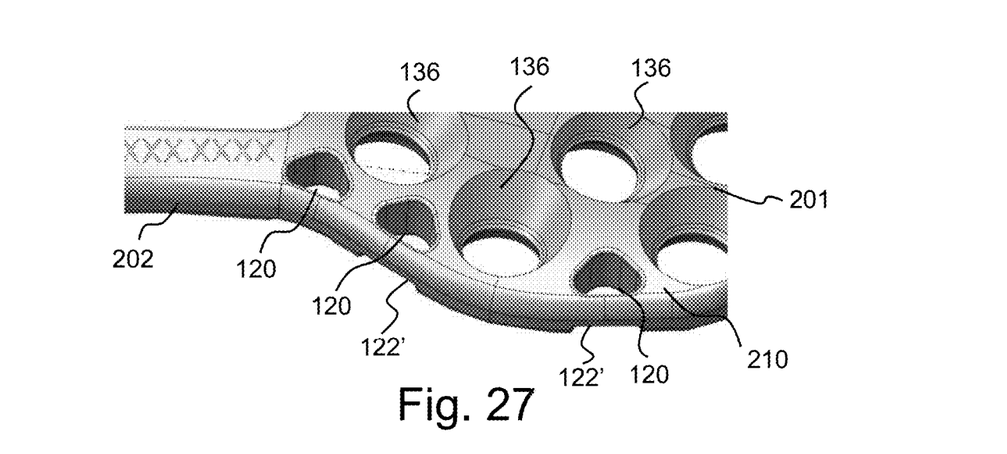
FIGS. 27 and 28 are top and bottom perspective views of a portion of the end of a superior fixation plate in accordance with an embodiment of the disclosure illustrating the k-wire/suture holes thereof.
Figure 28:
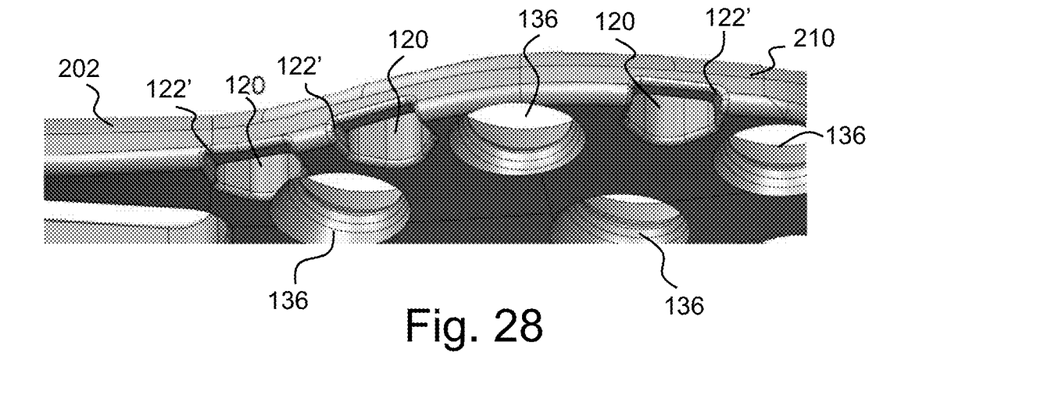
Figure 29:
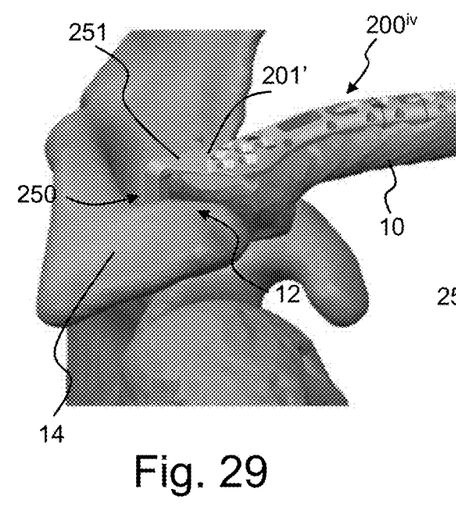
FIGS. 29 and 30 are front perspective views of a hook plate in accordance with an embodiment of the disclosure positioned relative a clavicle and AC joint, with FIG. 30 illustrating the clavicle and AC joint transparently.
Figure 30:
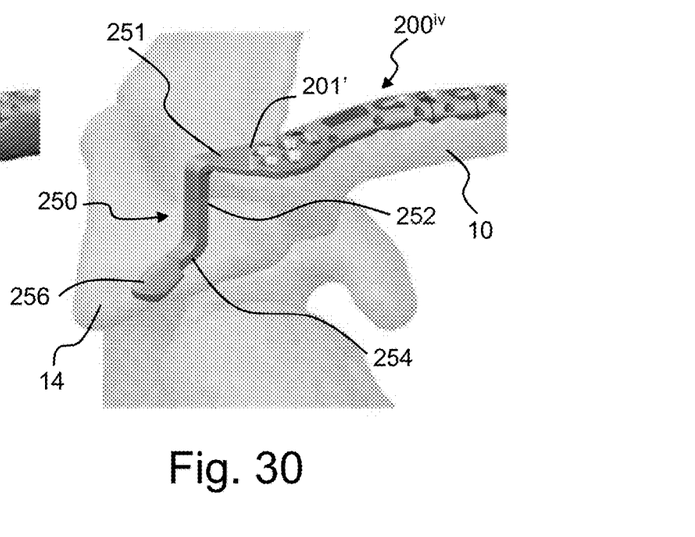
Figures 31, 32:
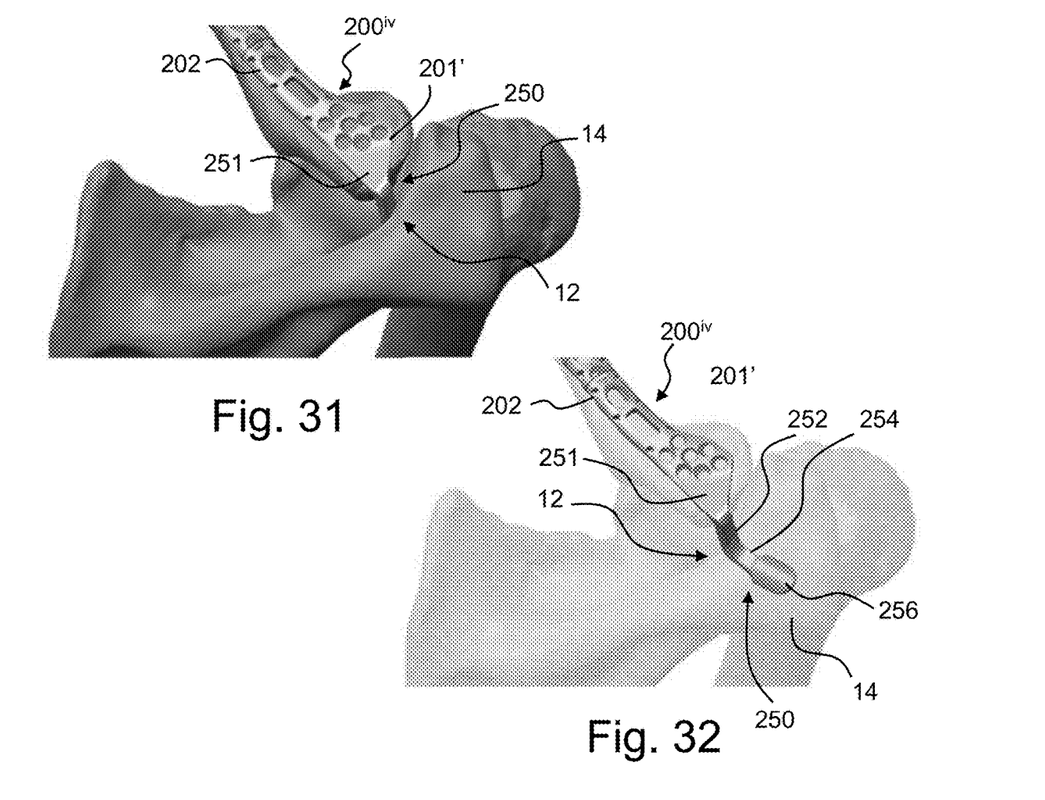
FIGS. 31 and 32 are top perspective views of the hook plate of FIG. 29, with FIG. 32 illustrating the clavicle and AC joint transparently.

Referring to FIGS. 22 and 25-28, the lateral superior fixation plate 200 includes a lateral extension 210. Such a plate 200 may be used, for example, to fix fractures occurring at the far lateral end of the clavicle 10. The lateral extension 210 contains a plurality of polyaxial holes 136 that allow many diverging screw trajectories to secure the plate in this thin, metaphyseal bone region, as shown in FIG. 26. The polyaxial holes 136 accept locking and non-locking screws. For ease of surgical planning, nominal, diverging and converging trajectories are intended to secure in regions of dense bone and away from the acromioclavicular joint space.

The lateral extension 210 also defines a plurality of oblong suture holes 120 similar to those in the shaft of the plate 200. The lateral extension suture holes 120 have undercuts 122' to allow free passage of suture underneath the plate 200, however, the width of these undercuts 122' is limited to the width of the suture hole 120.

Referring to FIGS. 29-34, a superior hook plate 200iv will be described. The body 202 of the superior hook plate 200iv is similar to the previous embodiments except that a hook member 250 extends from the end 201' of the plate 200iv. Such hook plates 200iv may, for example, be utilized to aid healing of acromioclavicular (AC) joint separations with clavicular displacement. The hook member 250 includes an extension portion 251 which extends from the end 201' of the plate 200iv to the postero-lateral side of the AC joint 12. A descending arm 252 extends inferiorly from the extension portion 251 to a given depth from which a lateral arm 254 angles laterally to hook underneath the acromion 14. This constrains superior displacement of the clavicle 10. The hook plates are offered with various descending arm 252 lengths to accommodate diverse shoulder and injury anatomies.

Figure 33:
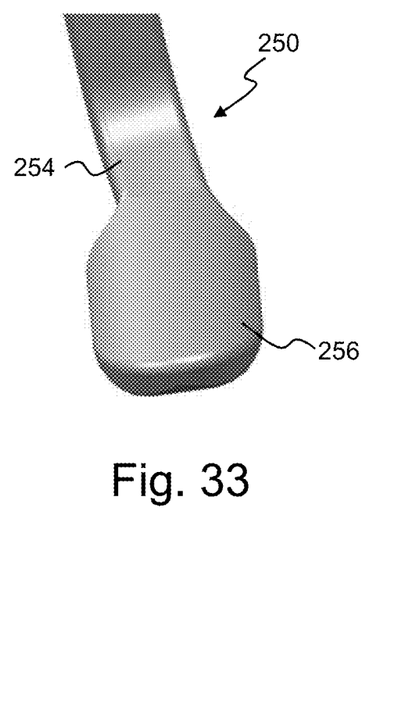
FIG. 33 is a perspective view of the hook portion of a hook plate in accordance with an embodiment of the disclosure.
Figure 34:
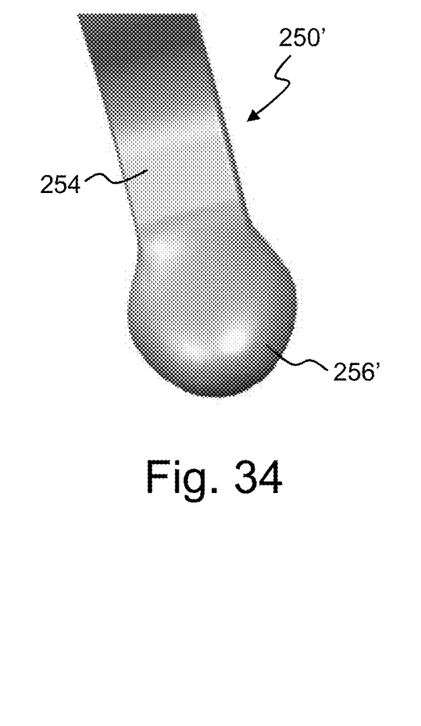
FIG. 34 is a perspective view of the hook portion of a hook plate in accordance with another embodiment of the disclosure.
Figure 35:
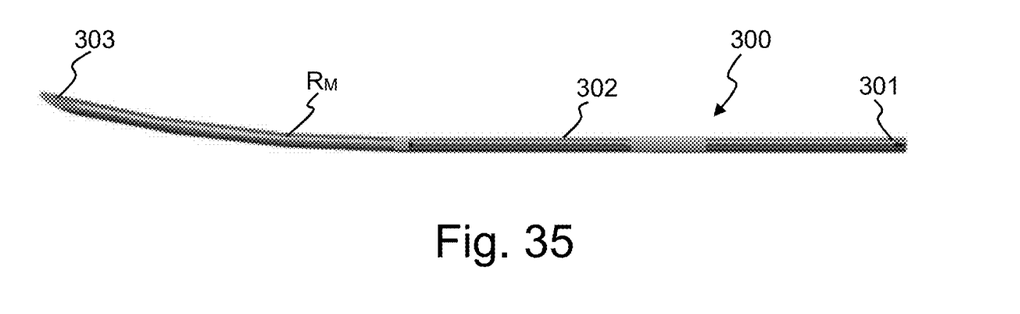
FIG. 35 is a side elevation view of an intramedullary clavicle nail in accordance with an embodiment of the invention.

In the present embodiment, the lateral arm 254 fans out into a widened head 256 that increases contact surface area between the hook member 250 and the underside of the acromion 14. The widened head 256 may have various shapes, with FIGS. 33 and 34 illustrating exemplary shapes. The widened head 256 in FIG. 33 has a curved spatula shape while the widened head 256' in FIG. 34 has a curved spoon shape, each with smoothed edges. The widened heads 256, 256' help to reduce painful irritation, bony erosion, and incidental fracture on the underside of the acromion 14 by distributing the load to a wider area. The smoothed edges of the widened head 256, 256' also facilitate insertion into this soft tissue space and eventual removal, and while in place minimizes irritation to the rotator cuff and other soft tissues.

Referring to FIGS. 35-39, an intramedullary clavicle nail 300 in accordance with an embodiment of the disclosure will be described. A plurality of different sized nails 300, for example, having diameters of 3.0, 3.5, 4.0, 4.5, and 5.0 mm, may be provided as a set. The nails 300 enable minimally invasive treatment of select clavicle fractures. Advantages of this technique are much less incision and scarring, and often elimination of soft tissue prominence.

Figure 39:
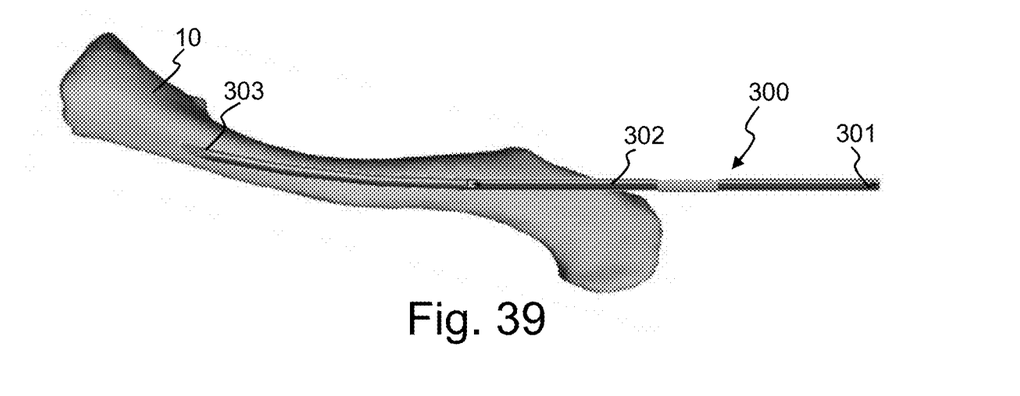
FIG. 39 is a side elevation view of the intramedullary clavicle nail of FIG. 35 positioned within the intramedullary of a clavicle.

Each nail 300 includes an elongated body 302 extending from a trailing end 301 to a medial, leading end 303. The nail body 302 has a pre-contoured configuration with anatomically appropriate radius $R_M$ at the medial, leading end 303. The body 302 transitions to a straight region at the trailing end 301. As shown in FIG. 39, upon insertion, the trailing end 301 of the nail 300 exits the posterolateral side of the clavicle 10. The nail 300 is then cut to length and tamped below the bone surface.

Figures 36, 37, 38:
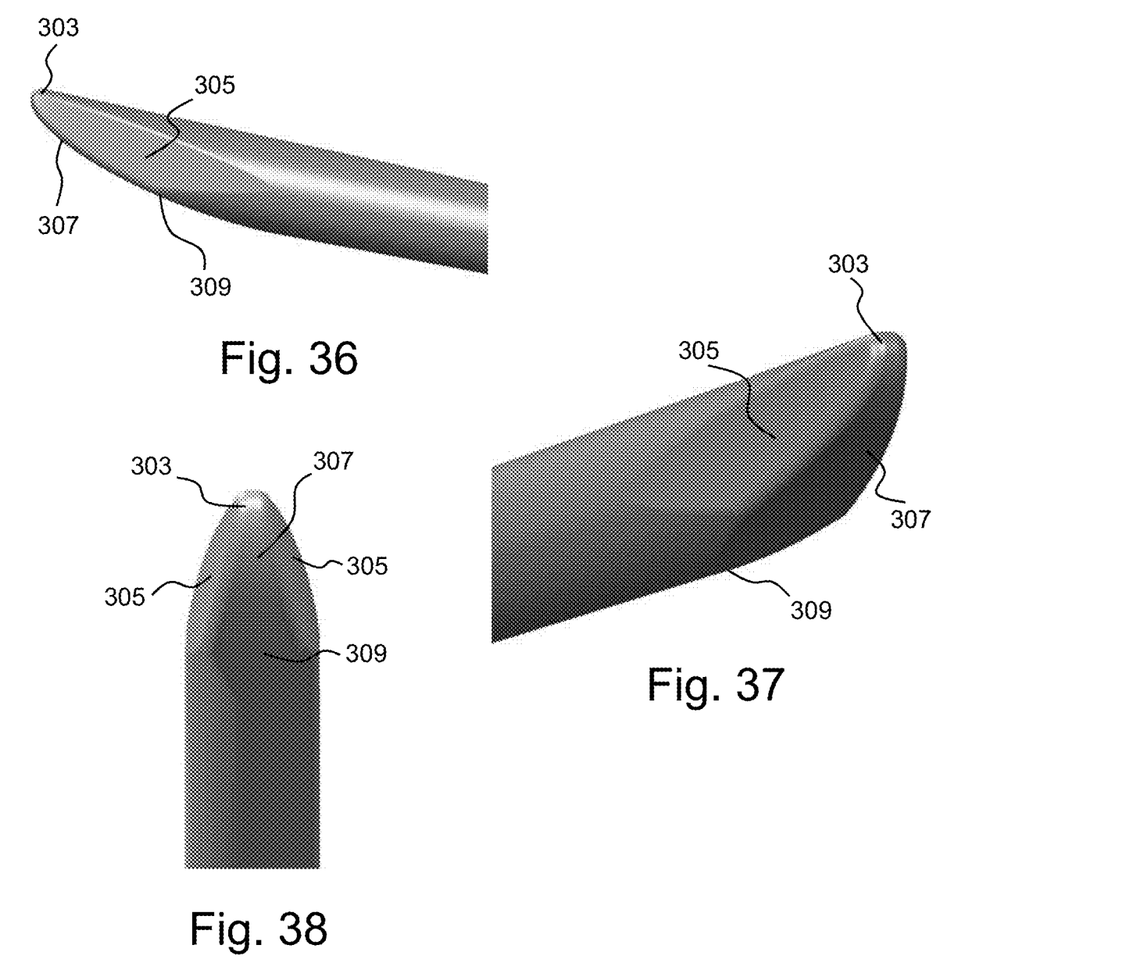
FIG. 36 is a left side perspective view of the tip portion of the intramedullary clavicle nail of FIG. 35.
FIG. 37 is a right side perspective view of the tip portion of the intramedullary clavicle nail of FIG. 35.
FIG. 38 is a bottom perspective view of the tip portion of the intramedullary clavicle nail of FIG. 35.

Referring to FIGS. 36-38, the leading end 303 of the nail 300 has a pointed shape with flats 305 on each side of a rounded tip 307. The rounded tip 307 extends to a wide underside 309. The pointed shape helps to advance the nail 300 in the medullary canal with minimal pre-drilling, while the wide underside 309 of the tip offers some width to rest against the canal wall. Such resistance helps to provide some rotational stability to maintain the orientation of the pre-curved nail with the restored anterior bone curvature.

The orthopedic bone plates, intramedullary nails, and systems may be particularly useful in in the treatment of the clavicle. The devices may be provided with anatomic shapes suitable for fixation at distinct regions of the clavicle. It is envisioned, however, that the features of one embodiment may be combined with features of another embodiment and the disclosure and associated technology can encompass other embodiments not expressly shown or described herein.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A clavicle fixation device comprising:
an elongated plate having an upper surface, an opposing lower surface, a first lateral side, a second lateral side, a first end and a second end and defining a central portion, a first end portion between the central portion and the first end, and a second end portion between the central portion and the second end, the elongated plate having a contour which is configured to complement a contour of a clavicle anterior or superior surface, the elongated plate defining a plurality of spaced apart screw holes,
wherein the first end portion narrows moving from the central portion to the first end,
wherein the lower surface is concavely curved from the first lateral side to the second lateral side, and
wherein the elongated plate defines a plurality of oblong suture holes along the first lateral side of the elongated plate and a plurality of oblong suture holes along the second lateral side of the elongated plate.

2. The clavicle fixation device according to claim 1 wherein the second end portion narrows moving from the central portion to the second end.

3. The clavicle fixation device according to claim 1 wherein the first end portion narrows in at least two different angles, with a first subportion closer to the central portion narrowing at a steeper angle than a second subportion closer to the first end.

4. The clavicle fixation device according to claim 1 wherein each of the end portions taper from a maximum thickness adjacent the central portion to a reduced thickness adjacent the each end portion.

5. The clavicle fixation device according to claim 4 wherein the central portion is sized such that the central portion is configured to overlie a common clavicle fracture zone which is determined based on image research study of clavicle fractures.

6. The clavicle fixation device according to claim 1 wherein the plurality of suture holes on the first lateral side of the elongated plate align with the plurality of suture holes on the second lateral side of the elongated plate.

7. The clavicle fixation device according to claim 6 wherein a pair of suture holes are axially aligned from one another on opposed edges of the elongated plate, the opposed suture holes axially positioned between adjacent screw holes.

8. The clavicle fixation device according to claim 7 wherein at least one elongated undercut is defined along an inner surface extending between the first and second ends, the elongated undercut having a radial or elliptical dimension smaller than a radial or elliptical dimension of the inner surface.

9. The clavicle fixation device according to claim 7 wherein at least two elongated undercuts are defined along an inner surface extending between the first and second ends, each elongated undercut having a radial or elliptical dimension smaller than a radial or elliptical dimension of the inner surface.

10. The clavicle fixation device according to claim 1 wherein an undercut in an inner surface of the elongated plate is aligned with each suture hole.

11. The clavicle fixation device according to claim 10 wherein at least a portion of the undercuts have a width larger than a width of the corresponding suture hole.

12. The clavicle fixation device according to claim 1 wherein the elongated plate defines an outer surface and an inner surface and at least the inner surface has a rounded configuration.

13. The clavicle fixation device according to claim 1 wherein the screw holes include polyaxial holes and dynamic compression plating slots.

14. The clavicle fixation device according to claim 1 further comprising a sliding slot screw having a shank with a first diameter and a head with a second diameter, and wherein the elongated plate defines a sliding slot having a width which is larger than the first diameter and smaller than the second diameter.

* * * * *